(12) United States Patent
Gross et al.

(10) Patent No.: US 9,946,843 B2
(45) Date of Patent: Apr. 17, 2018

(54) CLINICAL DECISION SUPPORT SYSTEM BASED TRIAGE DECISION MAKING

(71) Applicant: KONINKLIJKE PHILIPS N.V., Eindhoven (NL)

(72) Inventors: Brian David Gross, North Andover, MA (US); Joseph James Frassica, Gloucester, MA (US); Ivan Salgo, Pelham, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 195 days.

(21) Appl. No.: 15/034,609

(22) PCT Filed: Nov. 13, 2014

(86) PCT No.: PCT/IB2014/066005
§ 371 (c)(1),
(2) Date: May 5, 2016

(87) PCT Pub. No.: WO2015/071847
PCT Pub. Date: May 21, 2015

(65) Prior Publication Data
US 2016/0328525 A1 Nov. 10, 2016

Related U.S. Application Data

(60) Provisional application No. 61/903,438, filed on Nov. 13, 2013.

(51) Int. Cl.
*G06K 9/00* (2006.01)
*G06F 19/00* (2018.01)
(Continued)

(52) U.S. Cl.
CPC ........ *G06F 19/345* (2013.01); *A61B 5/02028* (2013.01); *A61B 5/14542* (2013.01);
(Continued)

(58) Field of Classification Search
CPC ............. G06F 19/3431; G06F 19/3481; A61B 5/0205; A61B 5/0022; A61B 5/7275;
(Continued)

(56) References Cited

U.S. PATENT DOCUMENTS

| | | | | |
|---|---|---|---|---|
| 4,957,115 A | * | 9/1990 | Selker | A61B 5/0452 600/509 |
| 2006/0247506 A1 | * | 11/2006 | Balberg | A61B 5/0097 600/323 |

(Continued)

FOREIGN PATENT DOCUMENTS

| | | |
|---|---|---|
| WO | 2004061744 A2 | 7/2004 |
| WO | 2008005480 A1 | 1/2008 |
| WO | 2013103885 A1 | 7/2013 |

OTHER PUBLICATIONS

Mahle, et al., Role of Pulse Oximetry in Examining Newborns for Congenital Heart Disease: A Scientific Statement from the AHA and AAP, American Academy of Pediatrics, vol. 124, No. 2, Aug. 2009, pp. 1-14.

(Continued)

*Primary Examiner* — Bhavesh Mehta
*Assistant Examiner* — Ian Lemieux (57) ABSTRACT

A method includes obtaining an electrical signal that includes a set of at least two sensed physiologic measurements of a patient, comparing the at least two physiologic measurements with a predetermined physiologic measurement range, identifying data required to determine a probability and a severity of a condition of interest of the patient, in response to determining the at least two physiologic measurements do not satisfy the physiologic measurement range, receiving the identified data in electronic format, determining a first probability and a first severity of the condition of interest based on the received identified data, determining a recommended course of action for the patient (Continued)

based on the first probability and the first severity, resources of a healthcare facility, and an event guideline; and causing a display to visually present the first probability and first severity and the recommended course of action.

18 Claims, 4 Drawing Sheets

(51) Int. Cl.
    *A61B 5/02*     (2006.01)
    *A61B 5/145*     (2006.01)
    *A61B 5/00*     (2006.01)
    *G06T 7/00*     (2017.01)

(52) U.S. Cl.
    CPC ............ *A61B 5/7275* (2013.01); *A61B 5/743* (2013.01); *G06F 19/321* (2013.01); *G06F 19/322* (2013.01); *G06F 19/327* (2013.01); *G06F 19/3431* (2013.01); *G06T 7/0014* (2013.01); *G16H 10/60* (2018.01); *G16H 40/20* (2018.01); *G16H 50/20* (2018.01); *G16H 50/30* (2018.01); *A61B 2503/045* (2013.01); *G06F 19/3443* (2013.01); *G06T 2207/10132* (2013.01); *G06T 2207/30048* (2013.01); *G06T 2207/30104* (2013.01); *G16H 50/70* (2018.01)

(58) Field of Classification Search
    CPC ......... A61B 5/002; A61B 5/412; A61B 5/742; A61B 5/411; A61B 5/7264; A61B 5/7282; A61B 2503/045; A61B 5/00; A61B 5/02; A61B 5/4842; A61B 5/7246
    See application file for complete search history.

(56) References Cited

U.S. PATENT DOCUMENTS

| | | | |
|---|---|---|---|
| 2006/0271408 A1* | 11/2006 | Rosenfeld | A61B 5/412 705/3 |
| 2006/0271410 A1* | 11/2006 | Rosenfeld | A61B 5/412 705/3 |
| 2008/0071155 A1 | 3/2008 | Kiani | |
| 2009/0216564 A1* | 8/2009 | Rosenfeld | A61B 5/411 705/3 |
| 2009/0281839 A1* | 11/2009 | Lynn | G06F 19/321 705/3 |
| 2012/0046532 A1 | 2/2012 | Chang et al. | |
| 2016/0143594 A1* | 5/2016 | Moorman | A61B 5/02405 705/2 |

OTHER PUBLICATIONS

Knowles, et al., "Newborn screening for congenital heart defects: a systematic review and cost-effectiveness analysis", Health Technology Assessment 2005, vol. 9, No. 44.

Granelli, "Pulse Oximetry: Evaluation of a potential tool for early detection of critical congenital heart disease", Department of Paediatrics, Institute of Clinical Science at Sahlgrenska Academy, University of Gothenburg, Sweden, 2009, pp. 1-80.

\* cited by examiner

CLINICAL DECISION SUPPORT SYSTEM BASED TRIAGE DECISION MAKING

CROSS-REFERENCE TO PRIOR APPLICATIONS

This application is the U.S. National Phase application under 35 U.S.C. § 371 of International Application No. PCT/IB2014/066005, filed on Nov. 13, 2014, which claims the benefit of U.S. Provisional Patent Application No. 61/903,438, filed on Nov. 13, 2013. These applications are hereby incorporated by reference herein, for all purposes.

The following generally relates to a clinical decision support (CDS) system and more particularly to a CDS system that determines a probability and a severity of a condition of interest of a patient and a healthcare recommendation based thereon.

Detecting certain rare clinical conditions can be difficult, and determining the severity of the condition may exceed certain clinicians' capabilities and expertise. In many situations the severity assessment is critical to determine if the patient can be safely cared for in the current care setting or needs to be transported to a facility with services typically needed for patients with such a severity. Examples of such condition are congenital cardiac defects in a newborn, which can be life threatening in the first hours and days of life.

Some congenital cardiac conditions require relatively immediate stabilization and intervention to prevent mortality. Other congenital heart conditions may present in the early neonatal period with very subtle or no obvious symptoms. Patients with these conditions are often discharged home as "normal" and deteriorate at home. Survival in these patients depends upon rapid identification, triage, resuscitation and intervention. In many cases, these late presenting congenital cardiac patients suffer profound and irreversible injury or death because of delays in intervention.

Guidelines on screening newborns attempt to improve detection of these congenital cardiac defects prior to discharge from the nursery through the use of pulse oximetry. Pulse oximetry may detect some critical congenital heart diseases such as Hypoplastic Left Heart Syndrome Pulmonary Atresia with intact septum Tetralogy of Fallot, Total Anomalous Pulmonary Venous Return, Transposition of the Great Vessels Tricuspid Atresia, and Truncus Arteriosus. These Critical Congenital Heart Diseases (CCHDs) represent non-limiting examples of congenital Heart defects.

Unfortunately, pulse oximetry may not, as reliably, detect other CCHDs such as aortic arch atresia or hypoplasia, interrupted aortic arch, coarctation of the aorta, double-outlet right ventricle, Ebstein's anomaly, pulmonary stenosis, atrioventricular septal defect, Ventricular Septal Defect, or single ventricle defects (other than hypoplastic left heart syndrome and tricuspid atresia), and infants with these conditions would benefit from early detection, triage and intervention.

Aspects described herein address the above-referenced problems and others.

The following describes an approach that facilitates early detection, triage and intervention of certain conditions of interest. In one instance, initial physiologic parameters are evaluated based on a "normal" range of a parameter guideline. If the physiologic parameters fall outside of the range, further data is obtained. A probability and a severity of a condition of interest are determined based at least on the obtained further data. Recommended healthcare is determined based on the probability and the severity and an event guideline. In one instance, the recommendation is to transport the patient to a healthcare or other facility for care. Optionally, the recommended healthcare includes healthcare suggestions that potentially mitigate worsening of the health status of the subject at the current facility are also provided. Optionally, the recommended healthcare results in control of an operation of an electrical device associated with the care of the patient.

In one aspect, a method includes obtaining an electrical signal that includes a set of at least two sensed physiologic measurements of a patient. The method further includes comparing the at least two physiologic measurements with a predetermined physiologic measurement range. The range is from a sensor output guideline, which is in electronic format. The method further includes identifying data required to determine a probability and a severity of a condition of interest of the patient. This is in response to determining the at least two physiologic measurements do not satisfy the physiologic measurement range. The method further includes receiving the identified data in electronic format. The method further includes determining a first probability and a first severity of the condition of interest based on the received identified data. The method further includes determining a recommended course of action for the patient based on the first probability and the first severity, resources of a healthcare facility, and an event guideline. The method further includes causing a display to visually present the first probability and first severity and the recommended course of action.

In another aspect, a system includes a computing system with at least one computer processor, input/output, and computer readable storage medium encoded with a triage module. The at least one computer processor, in response to executing instructions of the triage module, processes data received by the input/output and generates probabilities and severities of conditions of interest for a patient, generates a recommended course of action based on the probabilities and the severities, and causes a display to visually present the probabilities and severities and the recommended course of action.

In another aspect, a computer readable storage medium encoded with computer readable instructions, which, when executed by a processer, cause the processor to: compare a difference value of at least two physiologic measurements of the patient with a predetermined physiologic measurement range, wherein the at least two physiologic measurements correspond to blood oxygen concentration levels respectively sensed at a right foot of the patient and a left hand of the patient, identify an ultrasound imaging procedure for acquiring data to determine a probability and a severity of a condition of interest of the patient, in response to determining the difference value falls outside of the physiologic measurement range, receive image data from a scan based on the identified ultrasound imaging procedure, determine the probability and the first severity of the condition of interest based on the received image data, identify other data likely to improve an accuracy of the probability and the severity, update the probability and the severity in response to receiving at least a sub-set of the identified other data, determine a recommended course of action for the patient based on the updated probability, the updated severity, resources of the healthcare facility, and an event guideline, and visually present the updated probability and updated severity and the recommended course of action.

The invention may take form in various components and arrangements of components, and in various steps and arrangements of steps. The drawings are only for purposes of illustrating the preferred embodiments and are not to be construed as limiting the invention.

FIG. 1 schematically illustrates a clinical decision support system with a triage module.

Figure 1:
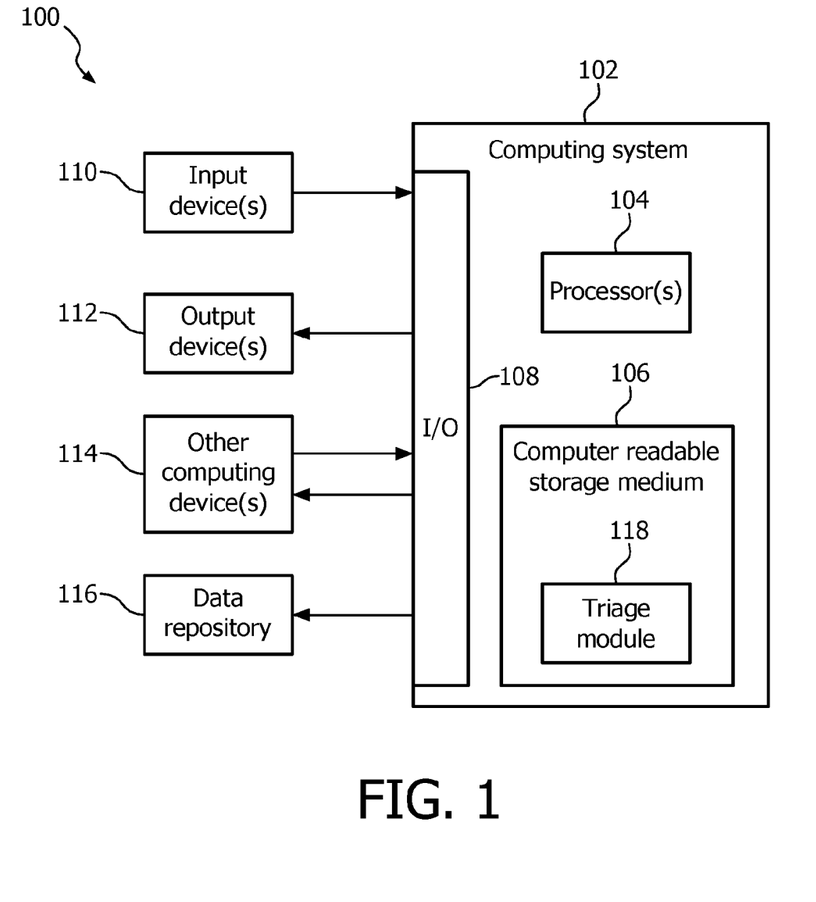

Initially referring to FIG. 1, a clinical decision support (CDS) system 100 is schematically illustrated. The CDS system 100 is implemented via a computing system 102. Examples of the computing system 102 include, but are not limited to, a stand-alone or dedicated computer, a physiologic monitoring apparatus, an imaging system, etc. In a variation, the CDS system 100 is part of an on-premise or "cloud" based computing environment, where processing algorithms are maintained and improved, for example, based on self-learning, or expert clinician adjudication of libraries, after the fact, including clinical diagnosis and outcome information.

The illustrated computing system 102 includes one or more hardware processors 104 (e.g., a central processing unit (CPU), a micro-processor (μ-processor), a controller, etc.) and computer readable storage medium 106 (which excludes transitory medium) such as physical memory encoded or embedded with computer readable instructions. The instructions, when executed by the one or more processors 104 cause the one or more processors 104 to carry out functions, such as one or more functions described herein and/or other functions.

Additionally or alternatively, the one or more processors 104 execute instructions carried by transitory medium such as a signal or carrier wave. In FIG. 1, the computer readable storage medium 106 is shown as a single element. However, it is to be appreciated that the computer readable storage medium 106 may include a plurality of separate hardware storage devices. The separate hardware storage devices include hardware storage devices local to the computing system 102, hardware storage devices external from the computing system 102, or hardware storage devices distributed between the computing system 102 and an external device(s).

Input/output (I/O) 108 receives information from one or more input devices 110 (e.g., a keyboard, a mouse, and the like) and/or conveys information to one or more output devices 112 (e.g., a display monitor, a printer, etc.). The I/O 108 is also configured to exchange data (in electronic format) with one or more other computing devices 114 and/or one or more data repositories 116. When configured to do so, the I/O 108 includes one or more physical-mechanical interfaces and/or a wireless interfaces for exchanging data. For example, the I/O 108 may include an RJ-45 connector, which electrically interfaces a connector of an Ethernet cable for data exchange over a wired network, a wireless network, transceiver for data exchange over a wireless network, etc. Examples of data exchanged include demographics, measured physiologic parameters, image data, laboratory results, clinician reports, observations, medical history, etc. Such data can be exchanged over the wired and/or wireless networks.

Examples of the computing devices 114 include, but are not limited to, an intravenous pump, an oxygen regulator, a ventilator, an ECG device, a communication device (e.g., a smartphone, a pager, etc.), a monitoring station (e.g., bedside, central, etc.), a computer, etc. Examples of data repositories 116 includes a picture archiving and communication system (PACS), a radiology information system (RIS), a hospital information system (HIS), an electronic medical record (EMR), a database, a server, an imaging system, a computer and/or other data repository. The data can be transferred via from a computing device 114 and/or a repository 116 in formats such as Digital Imaging and Communications in Medicine (DICOM), Health Level 7 (HL7), and/or other formats.

The I/O 108 may also be configured to exchange information such as notifications, messages, warning, etc, with an output device of the output devices 112 and/or a computing device of the computing devices 114. Such exchange can be through email, a text message, an instant message, a cell phone call, a pager page, etc.

The illustrated computer readable storage medium 106 stores software applications, software modules, and/or data. In the illustrated example, the computer readable storage medium 106 at least stores a triage module 118, which processes data received over the I/O 108. As described in greater detail below, in one non-limiting instance, the one or more processors 104, in response to executing the instructions of the triage module 118, evaluates health related information of a patient and recommends whether the subject should be transported to another healthcare facility for care based on the evaluation.

In one instance, the health state is determined by computing a probability and a severity for each of one or more conditions of interest. An example of computing such information is described in application Ser. No. 12/810,021, publication number US 2010/0312798 A1, which was filed on Dec. 8, 2008, and entitled "Retrieval of similar patient cases based on disease probability vectors," the entirety of which is herein incorporated by reference. Generally, application Ser. No. 12/810,021 discloses an algorithm that computes a probability and severity for certain conditions and updates the probability and severity based on new data.

In addition to recommending whether the subject should be transported to another healthcare facility for care, the one or more processors 104, in response to executing the instructions of the triage module 118, can further determine health care suggestions that potentially mitigate worsening of the health status of the subject at the current facility. The triage module 118 can further control an operation of an electronic device, of the other computer device(s), 114 associated with healthcare of the patient. The triage module 118 can further recommend other data types to obtain and evaluate. The one or more processors 104, in response to executing the instructions of the triage module 118, may also perform one or more other functions.

It is to be appreciated that the probability, the severity, and the recommendation, for example, facilitates early detection of difficult to detect acute diseases, such as acute congenital cardiac defects in a newborn, and application of suitable healthcare to the newborn. This may facilitate stabilizing a newborn, mitigating worsening of the condition, improving the chances of survival of the newborn, and mitagating irreversible injury or death. The probability, the severity, and the recommendation also facilitates early detection of other acute diseases and/or chronic diseases, which, likewise, may be difficult to detect, and benefits from early detection and suitable healthcare.

Figure 2:
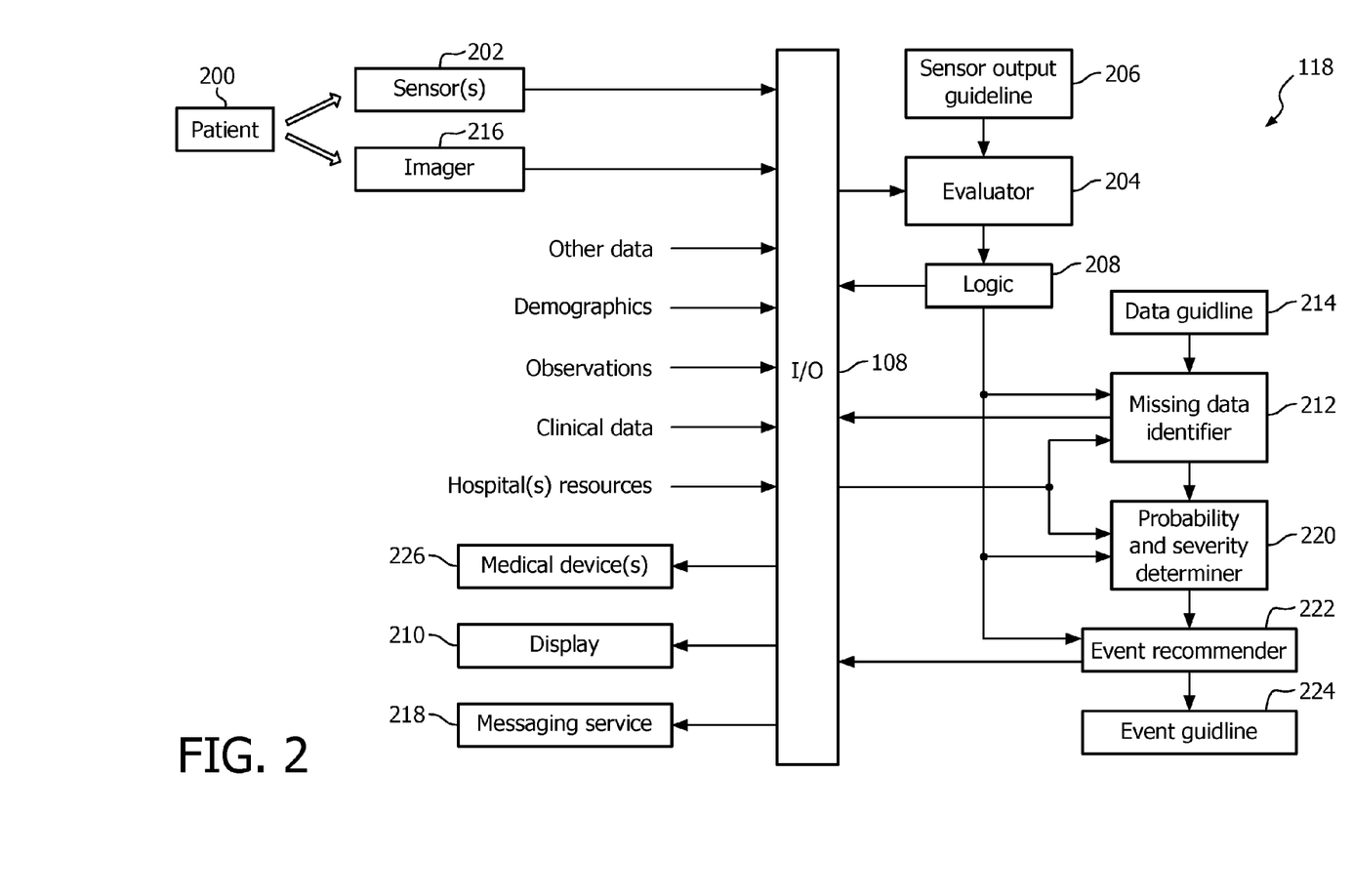
FIG. 2 schematically illustrates an example general triage module.

FIG. 2 schematically illustrates a non-limiting example of the triage module 118. In this example, the triage module 118 determines a probability and a severity of a condition of interest of a patient 200 and provides a recommended course of healthcare for the patient based thereon.

One or more physiologic sensors 202 sense physiologic signals of a patient. The one or more physiologic sensors 202 include at least one set of sensors that monitor a physiologic parameter that triggers the triage module 118 to determine the probability and the severity of the condition of interest and the recommendation.

An evaluator 204 evaluates the output signals of the at least one set of sensors. In one instance, this includes comparing the output signals in connection with a predetermined sensor output guideline 206, which indicates a "normal range." This includes, for example, comparing a difference between two sensor measurements of the same physiologic parameter, but sensed at different locations on the patient, with the guideline 206.

As utilized herein, the term "normal range" is a range deemed by a clinician(s), a medical facility, the medical community, etc. as indicating an absence of the condition of interest. The "normal range" is programmable and can be changed if the clinician(s), the medical facility, the medical community, etc. adopts a different range as the "normal range" or modifies the current "normal range."

Logic 208 receives the output of the evaluator 204 and determines whether to invoke other components of the triage module 118 to determine the probability and the severity of the condition of interest. For example, where the output signals are within the "normal range," the logic 208 does not invoke the other components of the triage module 118. Instead, the logic 208, in one instance, displays a message (in human readable format, via a display 210 device of the output devices 112, indicating the output signals are within the "normal range."

This may include displaying a numerical value indicative of the difference between two sensor measurements along with the "normal range," a textual message indicating absence of the condition, indicia such as color indicating absence or presence of the condition, etc. However, where the output signals are outside of the "normal range," the logic 208 invokes the other components of the triage module 118 to determine the probability and the severity of the condition of interest.

A missing data identifier 212, upon being invoked, determines, for the condition of interest, data needed to compute the probability and the severity of the condition of interest. In the illustrated example, the missing data identifier 212 compares the available data with a predetermined list of data in a guideline 214 to determine the missing data. The missing data identifier 212 displays a message (in human readable format), via the display 210 device of the output devices 112, indicating the missing data and/or suggesting particular procedure to acquire the missing data.

By way of this example, in one instance, the missing data identifier 212 identifies imaging data from an imager 216 as missing data, or data needed to compute the probability and the severity of the condition of interest. In this instance, the missing data identifier 212 conveys a signal to the display 210, which visually presents a message indicating certain contextual as well as image data is needed and/or suggests a particular type or imaging procedure to obtain the certain image data.

Subsequent to determining the probability and the severity, the missing data identifier 212 identifies other or additional data that may improve an accuracy of the probability and the severity of the condition of interest, which is used to update or compute another probability and severity. In the illustrated example, the other data includes, but is not limited to, data from other sensors, other imaging data, demographics, observations, clinical data, and/or other data.

Likewise, the missing data identifier 212 displays a message via the display 210 device indicating the additional missing data and/or suggesting a particular procedure to acquire the missing data. The signal requesting the initial missing date and the additional missing data can also be transmitted to a messaging service 218 of the output devices 112, which, for example, can send a message with this information through email, a text message, an instant message, a cell phone call, a pager page, a central station notification, etc.

A probability and severity determiner 220 determines the probability and the severity based on the currently available information. In response to receiving any additional missing data, the probability and severity determiner 220 determines an updated probability and severity. The determined probability and the severity are displayed via the display 210. Optionally, the messaging service 218 can be used to convey the probability and the severity to particular devices. After other or additional missing data is received, the probability and severity determiner 220 generates a signal indicating the updated and most recent probability and severity.

An event recommender 222 processes the probability and the severity in connection with hospital resources and a predefined event guideline 224, and generates an output signal that includes a recommended action for the patient. The action is, for example, a recommendation that the patient be transferred to another facility which is equipped to provide healthcare suitable for a patient with the probability and the severity of the condition of interest.

The action further suggests, for example, healthcare that should be provided at the current healthcare facility to mitigate worsening of the health status of patient. Where the current facility can provide the recommended healthcare, the recommendation is visually presented and/or provided personnel at the current healthcare facility. Similar to the probability and the severity, the recommended action can be displayed via the display 222 and/or conveyed to the messaging service 224.

The action may further include a control signal that controls an operation of one of more medical devices 226 of the other computing devices 114. For example, the action may include a control signal that turns on a monitoring feature of a monitor monitoring the patient, activates a bedside or central station monitor alarm, adjusts a flow rate parameter of an infusion (e.g., intravenous) pump, adjusts a regulator of an oxygen delivery system, etc. Generally, the action includes a control signal that controls an operation of an electrical device related to caring for the patient.

Figure 3:
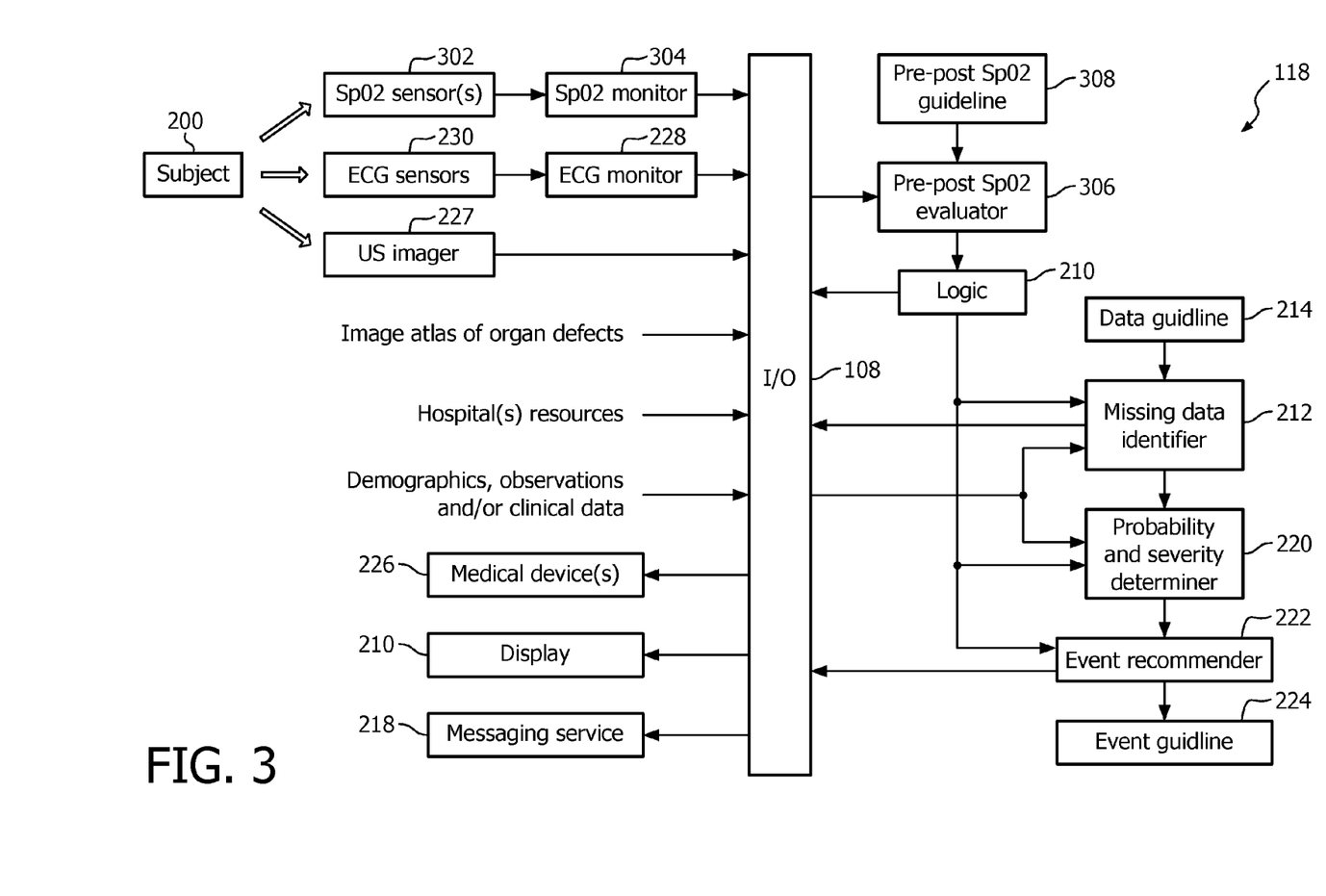
FIG. 3 schematically illustrates an example of the triage module in connection with congenital heart disease in a newborn.

FIG. 3 schematically illustrates a non-limiting example of the triage module 118 in connection with a specific condition of interest. In this example, the triage module 118 includes instructions for facilitating detection of congenital cardiac defects in newborns, triage and decision making such as whether to transport a newborn to a healthcare facility more equipped to address the congenital cardiac defects. For sake of brevity and clarity, other specific examples contemplated herein are not included in detail.

In the illustrated example, the I/O 108 of the computing system 102 receives blood oxygen signals respectively from at least two blood oxygen (SpO2) sensors 302. In this example, a first or one of the at least two SpO2 sensors 302 is located at a right foot of the subject, and a second or other one of the at least two SpO2 sensors 302 is located at a left hand of the subject. The at least two SpO2 sensors 302 concurrently measure blood oxygen for a same set of cardiac cycles, such as all or a sub-set of cardiac cycles.

The illustrated at least two SpO2 sensors 302 are, for example, part of a pulse oximeter, which indirectly monitors the oxygen saturation of a subject's blood and changes in blood volume in the skin, producing a photoplethysmogram. In a variation, the oxygen saturation is, for example, measured directly through a blood sample. In yet another variation, a combination of indirect and direct measurements are made using a pulse oximeter, blood sample and/or other approach to measuring blood oxygen saturation.

A SpO2 monitor 304 processes the signals from the at least two SpO2 sensors 302. Such processing, for example, includes pre-processing the signal to improve signal quality. The SpO2 monitor 304 determines and outputs a difference between the pre-processed blood oxygen measurement values (or a pre-post SpO2 value). Generally, the difference indicates whether blood is flowing through the lungs and being oxygenated or through a shunt and not being oxygenated. The SpO2 monitor 304 also measures other values such as, for example, a pulse transient time.

The illustrated triage module 118 includes a pre-post SpO2 evaluator 306 that receives and evaluates the pre-post SpO2 value. In the illustrated embodiment, the pre-post SpO2 evaluator 306 evaluates the pre-post SpO2 value based on a pre-determined pre-post SpO2 guideline that indicates a "normal" range for the pre-post SpO2 value, which is a range deemed by the medical community as indicating an absence of a congenital cardiac defect that would result in a newborn being transported to a different medical facility.

The logic, based on the signal from the evaluator 306, indicates that no further action is required (e.g., where the signal indicates the pre-post SpO2 value is within the "normal" range) or invokes further action (e.g., where the signal indicates the pre-post SpO2 value is outside of the "normal" range) of the other components of the triage module 118, as described in connection with FIG. 2 and/or otherwise.

In this example, the missing data identifier 212, upon being invoked, outputs a signal that indicates missing data required to generate the probability and severity of a congenital cardiac defect. The missing data identifier 212 determines the missing information based on the data guideline 214. The signal can be conveyed to the display 222 and/or messaging service, as described in connection with FIG. 2 and/or otherwise.

In the illustrated example, the missing data identifier 212 identifies ultrasound (US) image data from a scan of the newborn performed, for example, with an US imager 227. Generally, a suitable US imager is capable of providing feedback to a user as to the acceptability of imaging technique for assessment (such as 2D freehand, 2D with tracking device, mechanical 3D acquisition, electronic matrix array) of biometry like inter-cardiac shunt and gross anatomy assessment based on organ models.

The probability and severity determiner 212 determines a probability and severity a congenital cardiac defects based on the currently available information. The probability and severity determiner 212, for example, quantifies a probability of absence of congenital heart disease normalcy of the US image data with regards to probability and severity of congenital heart defects. In the illustrated example, this is achieved in part by processing the image data using the image atlas of organ defects, in connection with machine learning, to yield the probability and the severity of specific organ defects based on US image data.

The missing data identifier 212 also identifies an ECG of the newborn generated by an ECG monitor 228 based on electrical heat activity data sensed by ECG sensors 230 (3 lead, 12 lead, etc.). The missing data identifier 212 also identifies demographics, observations and clinical data, such as a presence and significance or cardiac murmur, acrocyanosis or central cyanosis, history of pregnancy, history of delivery, and other laboratory findings. As data becomes available, the probability and severity determiner 220 updates the probability and severity. The probability and severity determiner 220 also takes into account the SPO2 difference and/or other data obtained by the system.

The determined probability and the severity is output and displayed via the display 210, as described herein or otherwise. The displayed data provides, for example, guidance to the clinician as to the secondary investigations including additional sensor information, lab tests, other image procedures, and detailed physical exam input needed to refine the model findings. By way of example, the displayed data may indicate a list of congenital cardiac defects (e.g., defect A: 10%, defect B: 3%, etc.), and, for each defect provide a probability of the defect and a severity of the defect.

The event recommender 222 processes the probability and the severity based on the event guidelines 224 and generates an output signal that includes a recommended action for the patient. Where the triage module 118 determines the newborn has a congenital cardiac defect and that the present facility is not able to provide suitable care, the recommendation is to transport the newborn. The corresponding action may include, for example, notifying the transport service, controlling an electronic device associated with healthcare of the newborn, etc.

As discussed herein, the probability, the severity, and the recommendation facilitates early detection of difficult to detect acute diseases and application of suitable healthcare. With newborns and congenital cardiac defect, such care may stabilize the newborn, mitigating worsening of the condition, and improving the chances of survival of the newborn, and mitagating irreversible injury or death. Again, the probability, the severity, and the recommendation also facilitates early detection of other acute diseases and/or chronic diseases.

Figure 4:
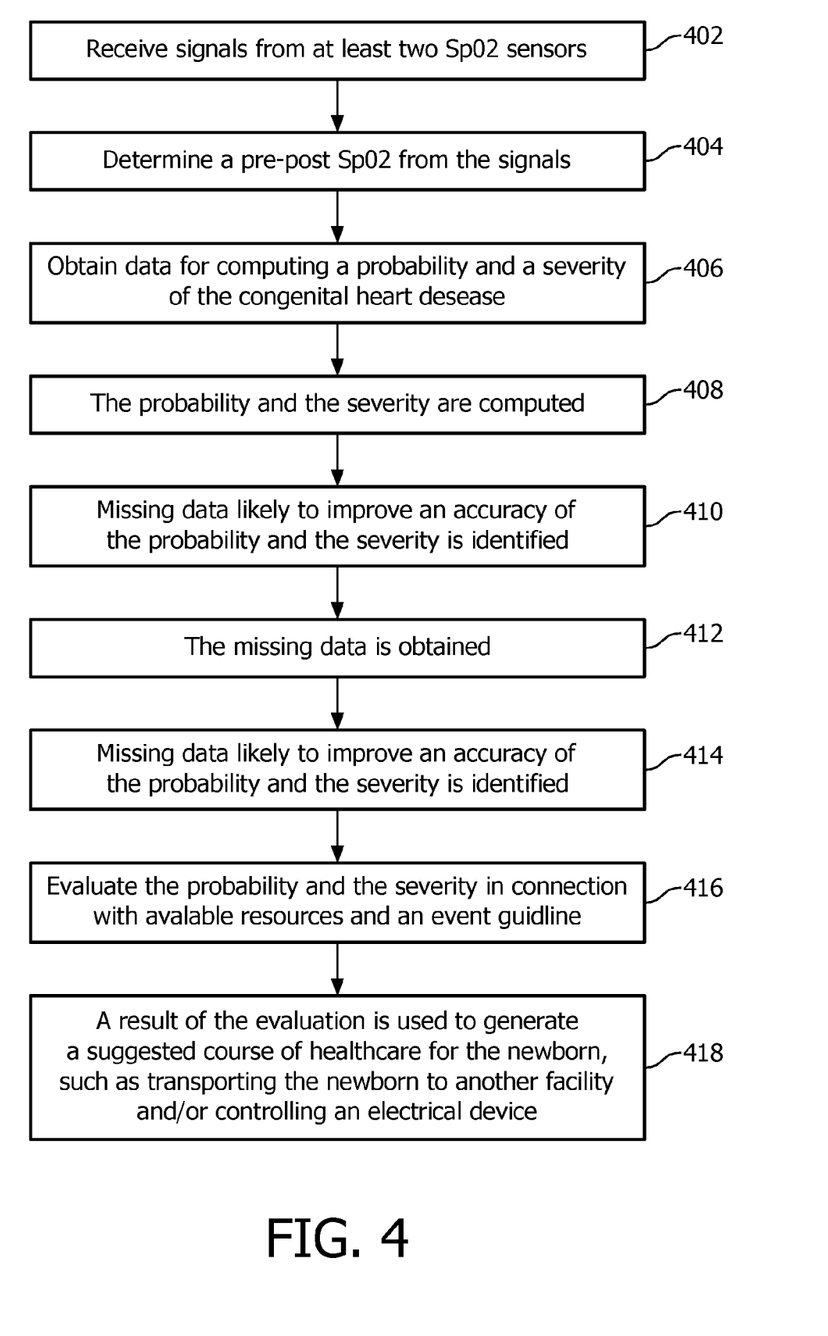
FIG. 4 illustrates a method for facilitating early detection, triage and intervention of certain conditions of interest.

FIG. 4 illustrates example method in accordance with the examples discussed herein. Similar to FIG. 3, FIG. 4 is discussed in connection with a particular example, congenital cardiac defects, for sake of brevity and clarity.

It is to be appreciated that the ordering of the acts of these methods is not limiting. As such, other orderings are contemplated herein. In addition, one or more acts may be omitted and/or one or more additional acts may be included.

At 402, signals from at least two SpO2 sensors, which simultaneously sense SpO2, are received.

As discussed herein, sensors located at a right foot and the left hand of the newborn provide information for determining whether blood is flowing through the lungs and being oxygenated as it is supposed to or is being shunted around the lungs and not being oxygenated.

At 404, the received signals are processed to determine a pre-post SpO2 difference value.

As discussed herein, this includes calculating a difference between two blood oxygen concentration measurements, measured at two right foot and left hand, respectively.

At 406, in response to the pre-post SpO2 value being outside of a range from a predetermined guideline, data for determining a probability and a severity of congenital heart disease is acquired.

As disclosed herein, in one instance, with congenital heart disease of a newborn, at least US imaging data is identified as being required for determining the probability and the severity.

At 408, the probability and the severity of congenital heart disease are computed based on the acquired data.

At 410, missing data likely to improve an accuracy of the probability and the severity is identified.

At 412, the missing data is obtained. This act is omitted where no missing data is identified and/or an operator determines not to acquire the identified missing data.

At 414, the probability and the severity of congenital heart disease are updated based on the obtained missing data.

At 416, the probability and the severity are evaluated in connection with available local healthcare resources and an event guideline.

At 418, a result of the evaluation is used to generate a suggested course of healthcare for the newborn.

As discussed herein, the suggested course of healthcare includes, for example, transporting the newborn to a different healthcare facility better equipped for the patient, healthcare to mitigate worsening of the health status of patient at the current healthcare facility, etc. The suggested course of healthcare may also include transmitting a control signal that controls an operation of at least one electrical device associated with the care.

The above acts may be implemented by way of computer readable instructions, encoded or embedded on computer readable storage medium, which, when executed by a computer processor cause the processor to carry out the described acts. Additionally or alternatively, at least one of the computer readable instructions is carried by a signal, carrier wave and other transitory medium and implemented by the computer processor.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A method, comprising:
receiving an electrical signal that includes a set of at least two sensed physiologic measurements of a patient;
comparing the at least two physiologic measurements with a predetermined physiologic measurement range from a sensor output guideline, which is in electronic format;
identifying an ultrasound imaging procedure for acquiring data to determine a probability and a severity of a condition of interest of the patient based on a data guideline, in response to determining the at least two physiologic measurements do not satisfy the physiologic measurement range;
obtaining image data from a scan based on the identified ultrasound imaging procedure;
determining the probability and the severity of the condition of interest based on the obtained image data;
determining a recommended course of action for the patient based on the probability and the severity, resources of a healthcare facility, and an event guideline; and
causing a display to visually present the probability and severity and the recommended course of action.

2. The method of claim 1, further comprising:
generating a control signal that controls an operation of an electronic device associated with healthcare for the patient based on the recommended course of action and the event guideline; and
controlling the operation of the electronic device with the control signal.

3. The method of claim 1, further comprising:
receiving an image atlas of organ defects, wherein the determining the probability and the severity of the condition of interest based on the obtained image data includes determining the probability and the severity of the condition of interest based on the image data and the image atlas of organ defects.

4. The method of claim 1, further comprising:
identifying other data likely to improve an accuracy of the probability and the severity of the condition of interest; and
updating the probability and the severity, based on the other data to generate an updated probability and an updated severity of the condition of interest;
wherein the recommended course of action is determined based on the updated probability and the updated severity, the resources of the healthcare facility, and the event guideline.

5. The method of claim 1, wherein the condition of interest is a congenital cardiac defect of a newborn and the at least two sensed physiologic measurements include a blood oxygen concentration sensed at a right foot of the newborn and a blood oxygen concentration sensed at a left hand of the newborn.

6. The method of claim 5, wherein comparing the at least two physiologic measurements includes taking a difference between the at least two physiologic measurements and determining a difference blood oxygen concentration value, comparing the difference blood oxygen concentration value with the measurement range from the sensor output guideline, and determining blood is being shunted around the lungs.

7. A computing system comprising:
at least one computer processor; and
a computer readable storage medium encoded with a triage module wherein the at least one computer processor is configured to execute instructions of the triage module to perform operations including:
receiving an electrical signal that includes a set of at least two sensed physiologic measurements of a patient;
comparing the at least two physiologic measurements with a predetermined physiologic measurement range from a sensor output guideline, which is in electronic format;
identifying an ultrasound imaging procedure for acquiring data to determine a probability and a severity of a condition of interest of the patient based on a data guideline, in response to determining the at least two physiologic measurements do not satisfy the physiologic measurement range;
obtaining image data from a scan based on the identified ultrasound imaging procedure;
determining the probability and the severity of the condition of interest based on the obtained image data;
determining a recommended course of action for the patient based on the probability and the severity, resources of a healthcare facility, and an event guideline; and
causing a display to visually present the probability and severity and the recommended course of action.

8. The system of claim 7, wherein the at least one computer processor is configured to control an operation of at least one electronic device based on the recommended course of action.

9. The system of claim 8, wherein the at least one computer processor is configured to further determine the probability and the severity based on the obtained image data and an image atlas of organ defects.

10. The system of claim 9, wherein the at least one computer processor is configured to further determine the probability and the severity based on physiologic sensor data, demographics, observations, and clinical data.

11. The system of claim 7, wherein the recommended course of action includes transporting the patient to another healthcare facility better equipped for the condition of interest.

12. The system of claim 11, wherein the recommended course of action further includes suggested healthcare to mitigate worsening of the condition of interest before the patient is transported.

13. The system of claim 7, wherein the recommended course of action includes suggested healthcare to mitigate worsening of the condition of interest at the healthcare facility using the resources available at the healthcare facility.

14. A non-transitory computer readable storage medium encoded with computer readable instructions, which, when executed by a processer, cause the processor to:
receive an electrical signal that includes a set of at least two sensed physiologic measurements of a patient;
compare the at least two physiologic measurements with a predetermined physiologic measurement range from a sensor output guideline, which is in electronic format;
identify an ultrasound imaging procedure for acquiring data to determine a probability and a severity of a condition of interest of the patient, in response to determining the at least two physiologic measurements do not satisfy the physiologic measurement range;
obtain image data from a scan based on the identified ultrasound imaging procedure;
determine the probability and the severity of the condition of interest based on the obtained image data;
determine a recommended course of action for the patient based on the probability and the severity, resources of a healthcare facility, and an event guideline; and
visually present the probability and severity and the recommended course of action.

15. The non-transitory computer readable storage medium of claim 14, wherein computer readable instructions further cause the processor to:
generate a control signal that controls an operation of an electronic device associated with healthcare for the patient based on the recommended course of action and the event guideline; and
control the operation of the electronic device with the control signal.

16. The non-transitory computer readable storage medium of claim 14, wherein computer readable instructions further cause the processor to:
receive an image atlas of organ defects, wherein the determining the probability and the severity of the condition of interest based on the obtained image data includes determining the probability and the severity of the condition of interest based on the image data and the image atlas of organ defects.

17. The non-transitory computer readable storage medium of claim 14, wherein computer readable instructions further cause the processor to:
identify other data likely to improve an accuracy of the probability and the severity of the condition of interest; and
update the probability and the severity, based on the other data to generate an updated probability and an updated severity of the condition of interest;
wherein the recommended course of action is determined based on the updated probability, the updated severity, the resources of the healthcare facility, and the event guideline.

18. The non-transitory computer readable storage medium of claim 14, wherein the condition of interest is a congenital cardiac defect of a newborn and the at least two sensed physiologic measurements include a blood oxygen concentration sensed at a right foot of the newborn and a blood oxygen concentration sensed at a left hand of the newborn.

* * * * *